(12) United States Patent
Singer et al.

(10) Patent No.: US 6,365,574 B2
(45) Date of Patent: Apr. 2, 2002

(54) ETHANOLATE OF AZITHROMYCIN, PROCESS FOR MANUFACTURE, AND PHARMACEUTICAL COMPOSITIONS THEREOF

(75) Inventors: Claude Singer, Kfar Sava; Judith Aronhime, Rehovot, both of (IL)

(73) Assignee: Teva Pharmaceutical Industries Ltd., Petah Tiqya ( * ) Notice: Subject to any disclaimer, the term of this patent is extended or adjusted under 35 U.S.C. 154(b) by 0 days.

(21) Appl. No.: 09/451,738

(22) Filed: Nov. 30, 1999

Related U.S. Application Data

(60) Provisional application No. 60/110,298, filed on Nov. 30, 1998.

(51) Int. Cl.⁷ .......................... A61K 31/70; C07H 1/00; C07H 17/08
(52) U.S. Cl. .......................... 514/29; 536/7.4; 536/18.5
(58) Field of Search .................. 536/7.5, 18.5; 574/29

(56) References Cited

U.S. PATENT DOCUMENTS

| 4,474,768 A | 10/1984 | Bright .......................... 514/25 |
| 4,517,359 A | 5/1985 | Kobrehel et al. ............ 536/7.4 |

FOREIGN PATENT DOCUMENTS

| CN | 1093370 | 12/1993 |
| EP | 0 298 650 | 1/1989 |
| WO | WO89/00576 | 1/1989 |

*Primary Examiner*—Elli Peselev
(74) *Attorney, Agent, or Firm*—Kenyon & Kenyon

(57) ABSTRACT

A novel, non-hygroscopic form of azithromycin is disclosed, as well as a method for preparing it by the gradual crystallization of azithromycin from ethanol by the addition of a minimal amount of water to effect crystal formation. Pharmaceutical compositions containing this novel form of azithromycin are also disclosed.

15 Claims, 2 Drawing Sheets

ETHANOLATE OF AZITHROMYCIN, PROCESS FOR MANUFACTURE, AND PHARMACEUTICAL COMPOSITIONS THEREOF

This application claims benefit of Ser. No. 60/110,298 filed Nov. 30, 1998.

FIELD OF THE INVENTION

This invention relates to a new ethanolate of azithromycin, processes for its manufacture, and pharmaceutical compositions containing the new ethanolate.

BACKGROUND OF THE INVENTION

Azithromycin, 9-deoxo-9a-aza-9a-methyl-9a-homoerythromycin A, having the formula

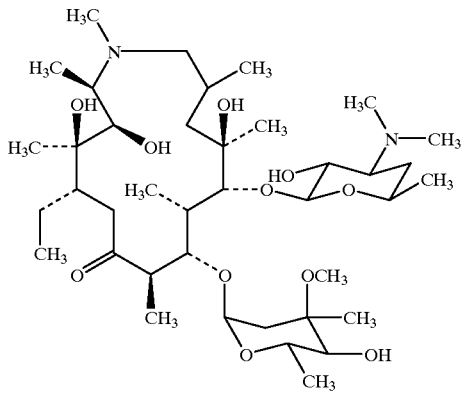

is a semi-synthetic macrolide antibiotic related to erythromycin A, useful for treating infections caused by susceptible microorganisms. This invention provides a new non-hygroscopic form of azithromycin, processes for its manufacture, and pharmaceutical compositions containing it.

Azithromycin may be made by methods described in U.S. Pat. Nos. 4,517,359 and 4,474,768. According to European Patent Application EP 298,650, the azithromycin obtained by these methods is a hygroscopic monohydrate. Because of its hygroscopic nature, this monohydrate is difficult to prepare and maintain in a form having a constant, reproducible water-content, and is particularly difficult to handle during formulation. EP 298,650 describes a dehydrate form of azithromycin that is less hygroscopic than the previously known monohydrate. The method described in EP 298,650 for making the dehydrate form is by crystallization from tetrahydrofuran, hexane and water.

Chinese Patent Application CN 1,093,370, describes an azithromycin crystal having water content of 4–6%. This form of azithromycin is stated as being less hygroscopic than the dehydrate described in EP 298,650. The method disclosed in CN 1,093,370 for making the described form of azithromycin is by crystallization from acetone and water.

SUMMARY OF INVENTION

The present invention provides a new ethanolate of azithromycin that is less hygroscopic than azithromycin monohydrate. The new ethanolate has an ethanol content of about 1.5% to about 3% and a water content of about 2% to about 4%.

The present invention also provides a method of making an ethanolate of azithromycin, comprising the steps of:

dissolving azithromycin in ethanol, adding water to the azithromycin solution such that crystallization of the azithromycin begins and a suspension is formed, and isolating the crystals of azithromycin.

The present invention further provides a pharmaceutical composition comprising a therapeutic amount of an ethanolate of azithromycin in accordance with the present invention and a pharmaceutically acceptable carrier.

DETAILED DESCRIPTION OF THE INVENTION

Figure 1:
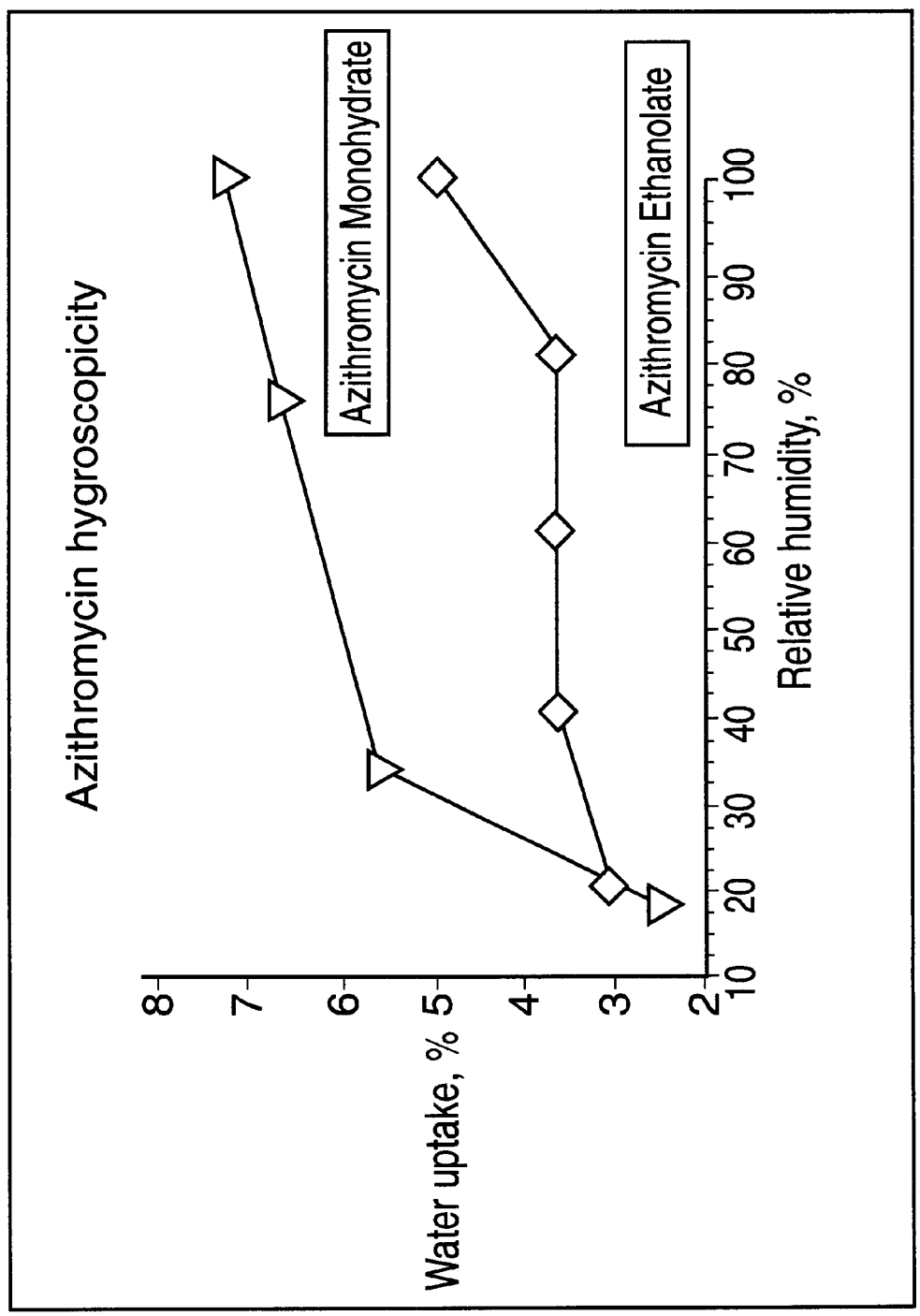
FIG. 1 is a comparison of hygroscopicity of the azithromycin ethanolate of the present invention and azithromycin monohydrate over a range of relative humidity, based upon data provided in EP 298,650.

The present invention discloses a new ethanolate of azithromycin that is less hygroscopic than the prior art monohydrate, and has an ethanol content of about 1.5 to about 3% and water content of about 2 to about 4%. Preferably the ethanol content is between about 1.5% and about 2.5%. Preferably the water content is between about 2.5% and about 3.5%. A comparison of the hygroscopicity of the ethanolate of the present invention and azithromycin monohydrate can be found at FIG. 1.

The process for manufacture of azithromycin ethanolate of the present invention utilizes the fact that water is a poorer solvent for azithromycin than ethanol, so that the addition of water to a solution of azithromycin in ethanol causes crystallization. Second, heating a solution of azithromycin in ethanol in the presence of water promotes crystallization.

In accordance with the process aspects of the invention, azithromycin is dissolved in absolute ethanol, in a ratio of about 2.5:1 (ethanol:azithromycin by weight) at a temperature of between about 10° C. and about 80° C., preferably at about 20° to about 30° C. A minimal amount of water is added, i.e. an amount no greater than 20% (by weight versus ethanol), preferably about 6 to about 16%. The solution is heated slowly at a constant temperature gradient over a first time interval of about 2 to about 18 hours, preferably about 3 to about 8 hours, reaching a maximum temperature of about 30 to about 80° C. and preferably about 40 to about 60° C. at the end of the first time interval. Crystallization appears to begin in the temperature range of about 30–45° C. During the first time interval, the water content of the solution is gradually increased, but to a concentration of no more than about 50%.

At the end of the first time interval, the resulting suspension is maintained at the maximum temperature for a second time interval of about 1 to about 18 hours, preferably about 1 to about 4 hours. During the second time interval, additional water is added to complete the crystallization process.

At the end of the second time interval, the suspension is cooled using a constant temperature gradient over a third time interval of about 1 to about 18 hours, preferably about 2 to about 4 hours, reaching a final temperature of about 20° C. The resulting precipitate is collected by filtration and dried to constant weight. Table 1 shows the water content of the new azithromycin ethanolate using Karl Fisher analysis and ethanol content using gas chromatography.

TABLE 1

Ethanol and Water Content of Azithromycin Ethanolate

| Batch | Ethanol Content (gas chromatography) % w/w (weight/weight) | Water Content (Karl-Fischer) % w/w |
|---|---|---|
| A | 2.2 | 3.24 |
| B | 2.3 | 2.46 |
| C | 2.2 | 2.71 |
| D | 2.3 | 2.77 |
| E | 2.2 | 3.28 |
| F | 1.52 | 2.70 |
| G | 1.7 | 3.40 |

In accordance with the present invention, the new ethanolate of azithromycin may be prepared as pharmaceutical compositions that are particularly useful for the treatment of infections caused by susceptible microorganisms. Such compositions comprise the new ethanolate of azithromycin with pharmaceutically acceptable carriers and/or excipients.

For example, these compositions may be prepared as medicines to be administered orally, parenterally, rectally, transdermally, bucally, or nasally. Suitable forms for oral administration include tablets, compressed or coated pills, dragees, sachets of powder for reconstitution, hard or gelatin capsules, sub-lingual tablets, syrups and suspensions. Suitable forms for parenteral administration include an aqueous or non-aqueous solution or emulsion, while for rectal administration suitable forms include suppositories with hydrophilic or hydrophobic vehicles. For topical application the invention provides ointments or aerosol formulations known in the art; for transdermal delivery there are provided suitable delivery systems as known in the art. For nasal delivery there are provided suitable aerosol delivery systems known in the art.

Experimental Details

Hygroscopicity profiles were obtained by maintaining samples in controlled humidity chambers for a period of two weeks, followed by Karl Fisher analysis of water content.

Gas chromatograms were obtained using a Hewlett-Packard 5890 gas chromatograph.

Powder x-ray diffraction patterns were obtained by methods known in the art using a Philips X-Ray powder diffractometer, Goniometer model 1050/70 at a scanning speed of 2° per minute, with a Cu radiation of $\lambda=1.5418$ Å.

This invention will be better understood from the Example that follows. However, the examples illustrate, but do not limit, the invention. Those skilled in the art will readily appreciate that the specific methods and results discussed are merely illustrative of the invention as described more fully in the claims that follow thereafter.

EXAMPLE

Preparation of Azithromycin Ethanolate.

Ten g of azithromycin crude was introduced into a 0.25 liter three-necked flat flanged jacketed vessel equipped with a mechanical stirrer, a condenser and thermometer and containing 30 ml of absolute ethanol at 20° C. Three ml of water at 20° C. were added and the solution was heated at a constant temperature gradient so as to reach 55° C. after 4 hours. Between 35° C. and 55° C., additional water having a total volume of 11 ml was slowly added at regular time intervals. When 55° C. was reached, the resulting suspension was maintained at this temperature for 2 hours, during which an additional 49 mL of water was added. The suspension was then cooled from 55° C. to 20° C. over 2 hours. The precipitate was filtered. After drying, 9 g of azithromycin ethanolate were obtained.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

We claim:

1. An ethanolate of azithromycin having an ethanol content of about 1.5% to about 3%.

2. The ethanolate of claim 1, having a water content of about 2% to about 4%.

3. The ethanolate of claim 2, wherein the water content is between about 2.5% and about 3.5%.

4. The ethanolate of claim 1, wherein the ethanol content is about 1.5% to about 2.5%.

5. The ethanolate of claim 4, wherein the water content is about 2% to about 4%.

6. The ethanolate of claim 5, wherein the water content is between about 1.5% and about 2.5%.

Figure 2:
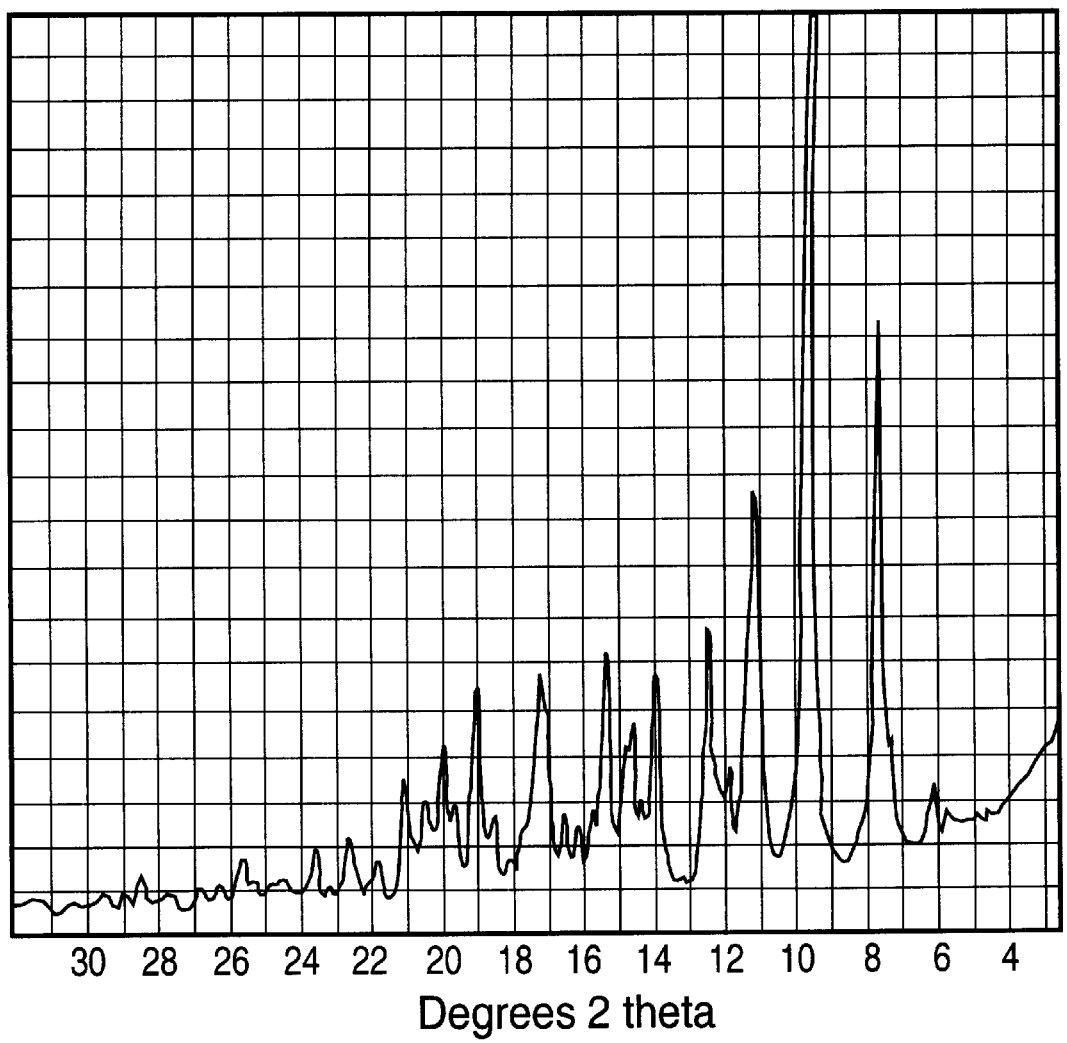
FIG. 2 is a characteristic powder X-ray diffraction pattern of the azithromycin ethanolate of the present invention.

7. An ethanolate of azithromycin that is characterized by a powder x-ray diffraction pattern substantially as depicted in FIG. 2.

8. A method of making an ethanolate of azithromycin, comprising the steps of:

forming an azithromycin solution by dissolving azithromycin in ethanol;

adding water to the azithromycin solution such that crystallization of the azithromycin begins and a suspension is formed; and, isolating the crystals of azithromycin.

9. The method of claim 8, further comprising maintaining the suspension at a temperature from about 30° C. to about 80° C. for a period of time, following the step of adding water to the azithromycin solution.

10. The method of claim 8, further comprising adding additional water to the suspension, and maintaining the suspension at a temperature from about 30° C. to about 80° C. for about 1 hour to about 18 hours, following the step of adding water to the azithromycin solution.

11. The method of claim 8, further comprising cooling the suspension to about 20° C., prior to the step of isolating the crystals of azithromycin.

12. The method of claim 8, wherein the ethanolate of azithromycin has an ethanol content of about 1.5% to about 3%.

13. The method of claim 8, wherein the ethanolate of azithromycin has a water content of about 2% to about 4%.

14. The method of claim 8, wherein the ethanolate is characterized by a powder x-ray diffraction pattern substantially as depicted in FIG. 2.

15. A pharmaceutical composition comprising a therapeutically effective amount of the ethanolate of the claim 1 and a pharmaceutically acceptable carrier.

* * * * *